United States Patent [19]

Nestor et al.

[11] 4,205,681

[45] Jun. 3, 1980

[54] INSTRUMENT FOR CLOSED COMPRESSION RUPTURE OF CONTRACTED FIBROUS CAPSULE SURROUNDING BREAST IMPLANT

[76] Inventors: Jack Nestor, 110 1st Ter., San Marino Island, Miami Beach, Fla. 33139; Gilbert B. Snyder, 6525 SW. 135th Dr., Miami, Fla. 33156

[21] Appl. No.: 10,509

[22] Filed: Feb. 7, 1979

[51] Int. Cl.² .............................................. A61B 17/28
[52] U.S. Cl. ..................................... 128/321; 128/319
[58] Field of Search .................. 128/303 R, 346, 321, 128/59–61, 68, 345, 1 R, 92 EA, 319; 81/3.4, 3.44, 3.34, 425 A, 425 R; 294/118, 28

[56] References Cited

U.S. PATENT DOCUMENTS

| | | | |
|---|---|---|---|
| 205,457 | 6/1878 | Woodruff | 81/3.44 |
| 253,269 | 2/1882 | Dowling | 81/3.44 X |
| 2,952,175 | 9/1960 | Edlen et al. | 81/425 R X |
| 3,134,281 | 5/1964 | Mintz | 81/3.44 |

*Primary Examiner*—Robert W. Michell
*Assistant Examiner*—Michael H. Thaler
*Attorney, Agent, or Firm*—Erwin M. Barnett

[57] ABSTRACT

A plurality of the elongated grippers are mounted in spaced apart, axially parallel, relation to project perpendicularly from opposing, substantially semi-circular, jaws of a pair of blades pivoted at a midportion thereof in scissor-fashion. A pair of lever arms are pivotally connected at one end and have handle portions formed at opposite ends thereof, said blades being symmetrically mounted between said lever arms with one end of each of the blades opposite said jaws pivotally attached to one of the lever arms for actuation thereby and for providing a mechanical advantage to close the jaws on application of a manual force applied to the handle portions. This closing brings the grippers of each jaw toward each other providing a compressive force on a breast requiring closed compression rupture when positioned therebetween.

7 Claims, 5 Drawing Figures

INSTRUMENT FOR CLOSED COMPRESSION RUPTURE OF CONTRACTED FIBROUS CAPSULE SURROUNDING BREAST IMPLANT

BACKGROUND OF THE INVENTION

1. Field of the Invention

This invention relates to the closed compression technique for rupturing a contracted fibrous capsule after augmentation mammaplasty and more particularly is directed to an instrument in the form of a manually operated compressor capable of achieving the initial "pop" in performing said technique.

2. Description of the Prior Art

A common complication after augmentation mammaplasty, whereby a coated silicone gel prosthesis is implanted through a submammary incision, is the development of excessive firmness, usually due to contraction of the fibrous capsule surrounding the prosthesis and producing a more spherical configuration. This condition becomes uncomfortable for the patient to lie on and is a possible source of embarrassment when touched. The cause of the condition is believed to be a problem of scar contraction, in these cases being a 3-dimensional spheroidal scar. This complication may be corrected by a surgical procedure, namely, a capsule release, which divides the capsule circumferentially near its base, involving the risks and disadvantages of surgery coupled with the possibility of the formation and contraction of a second capsule at a later date, again requiring surgical intervention.

As reported in an article by Baker, J. L. Jr., Bartels, R. J. and Douglas, W. M. in Plastic & Reconstructive Surgery, 1976, Vol. 58, Pages 137-141, by an odd coincidence, a patient having had augmentation mammaplasty and presenting this excessive firmness of the breast unilaterally was scheduled for an operative capsule release. Subsequently, the patient reported having been hugged by a large professional football player and squeezed very tightly, whereupon a loud popping sound was heard. Upon later examination, the patient found the excessively firm breast had become soft, which condition was confirmed by the surgeon in finding the breast soft and non-tender and showing no evidence of ecchymosis, hematoma, or other complication and, therefore, not requiring the scheduled surgery. Based on this report and findings, subsequent trials duplicating this squeeze technique were performed by the surgeon on other patients and proved successful. The technique developed for this purpose involves grasping the breast circumferentially in both hands in strangle-hold fashion and applying a circumferential compressive force by squeezing with the fingers until an initial "pop" is heard indicating the rupture of the capsule and thereafter a follow-through twist is applied to effect complete release of the implant circumferentially rather than a localized tear through which the implant may extrude into one of the quadrants of the breast to produce a dumbbell-shaped distortion.

A difficulty arises in supplying the force required to achieve this initial "pop", relative little force being required for the follow-through. Not only is sufficient strength in the fingers and hands of the operator often lacking to perform the strangle-hold technique, but the force exerted may result in damage to the operator's thumbs or fingers which is highly undesirable to any surgeon performing the technique. Other hand techniques have been utilized, for example, the palm compression or nut-cracker method, wherein the fingers are interlocked and pressure applied on opposite sides of the breast by the heels of the palms, and the closed fist crush, wherein the breast is positioned between clenched fists held either knuckles up or down and a squeezing force applied parallel to the chest wall utilizing the greater power of the pectoral and upper arm muscles of the operator as compared to the muscles of the forearm used in performing the strangle-hold method. Both these other techniques have been found to be awkward and unreliable by failing to ensure the proper grasping and surrounding of the base of the implant, as is accomplished in the strangle-hold technique, to produce the intracapsular force needed to rupture the capsule. For example, in the palm compression method, the hands may be too small to encompass the base of the implant, while in the closed fist crush it is difficult to maintain the fists in position in close proximity to the chest wall while applying the necessary force parallel to the chest wall. Thus, both these techniques, where greater force is available, experience difficulty in preventing the undesirable shifting of the implant in a direction at right angles to the application of the force.

Since the ability to stop short, that is, to exercise control of movement, appears to decrease to perhaps a vanishing point as the exerted force approaches a maximum capability of the muscles, there is also a significant danger, particularly in the nut-cracker and closed fist crush, of the operator applying excessive force and thereafter not being able to stop in time, whereby the coating or skin of the silicone gel may also rupture and require prompt remedial surgery.

There is, therefore, a current need for a reliable means for performing the closed compression method which will provide the advantages of the circumferential application of compressive force of the strangle-hold technique and will develop superior force exceeding that of the other techniques while eliminating the drawbacks and problems hereinbefore mentioned.

SUMMARY OF THE INVENTION

Among the objects of the invention is to provide an instrument, that is, a manually operated compressor, which shall satisfy the above outlined existing need in performing the closed compression technique and particularly for achieving, with ease and in an efficient and foolproof manner, the initial "pop", signifying rupture of the contracted fibrous capsule surrounding the augmentation mammaplasty implant.

The instrument features pincers mounted in symmetrical relation between a pair of actuating lever arms which are pivotally interconnected at one end, disposed in angular relation, and have opposite free ends serving as handles for operatively holding the instrument in both hands. The pincers comprises a pair of blades pivotally connected at a midportion thereof in scissor-fashion. One end of each blade is formed as a semi-circular jaw. A plurality of elongated grippers are mounted on each of the jaws to project perpendicularly from a designated rear side, that is, the side facing the patient when the instrument is in operative position, the grippers being arranged in parallel spaced relation to define a substantially circular opening sized to circumferentially fit the base of an implant in a patient's breast when the jaws of the pincers are in open position. The grippers which are mounted on the rear jaw are spaced along the arcuate length thereof, while those on the other jaw are longer and are located only along half the arcuate length thereof adjacent the pivotal connection between the blades permitting the jaws to close in overlapping relation to a predetermined extent. This jaw closing reduces the area of the opening as defined by the jaws and grippers enabling a circumferential compressive force, developed by operation of the handles, to be exerted upon the patient's breast at the base of the implant when the free ends of the grippers, which are substantially in a coplanar alignment, are positioned against the chest, locating the breast in the opening within the peripheral confines of the grippers.

The end of each blade opposite the semi-circular jaw is pivotally connected to one of the actuating lever arms at predetermined distances from the pivotal interconnection of the arms and from the pivotal connection of the blades to provide a mechanical advantage resulting in a relatively larger force being exerted by the grippers through the jaws as compared to that exerted at the handles, which are positioned in spaced relation for convenient and comfortable grasping by the operator's hands to exert a force easily supplied by the arms and shoulders urging the hands downwardly and toward each other in the operation of the instrument.

DESCRIPTION OF THE PREFERRED EMBODIMENT

Figure 1:
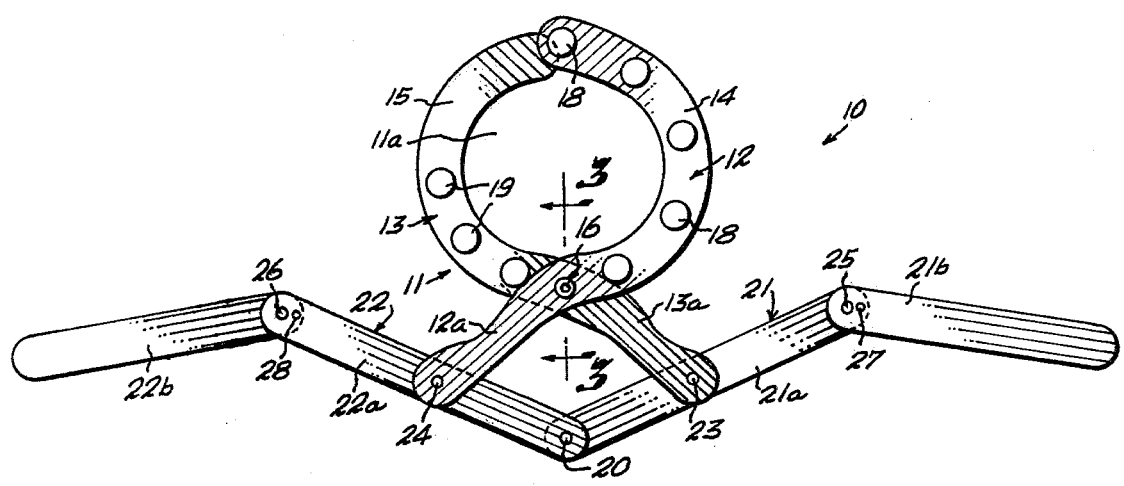
FIG. 1 is a rear elevational view of the manually operated compressor constructed to embody the invention shown with the pincers and grippers carried thereby in a fully open position.

Referring in detail to the drawing, 10 generally denotes the surgical instrument, constructed to embody the invention and more specifically herein designated as a manually operated compressor, seen to comprise pincers 11 mounted on and in symmetrical relation between a pair of actuating lever arms 21 and 22 which are pivotally connected at one end thereof by pivot pins 20.

Figures 2, 4:
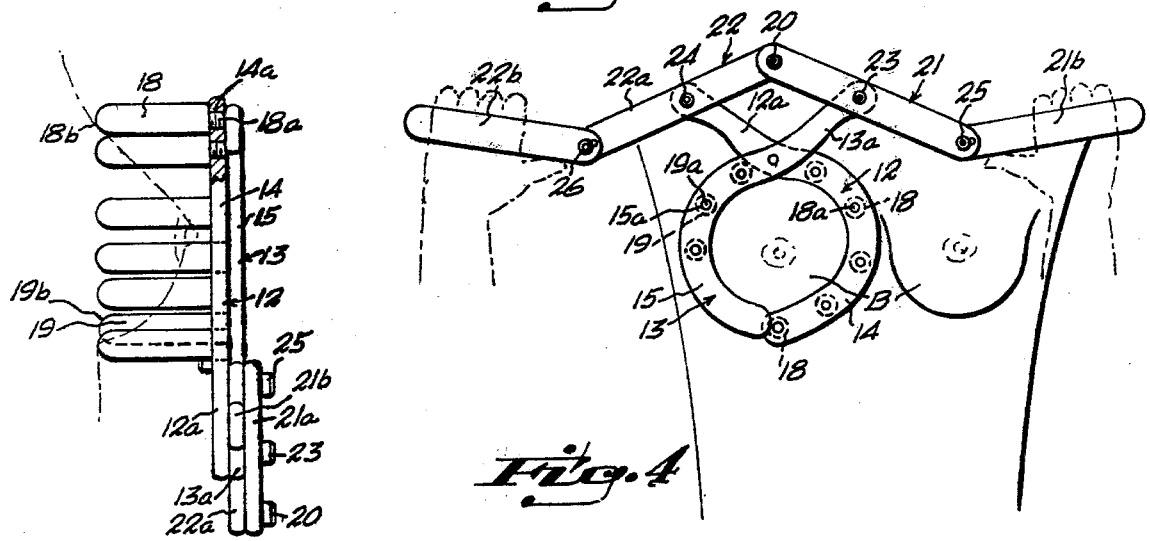
FIG. 2 is a side elevation view of the compressor as seen from the right side in FIG. 1 with parts broken away to show the threaded connection between the grippers and the supporting blade, an outline of a patient's body being shown in broken lines indicating the location of the breast when the grippers are in operative position with the ends thereof against the rib cage.
FIG. 4 is a front elevational view of a patient's trunk showing the compressor applied to the right breast in an open position preparatory to application of force to rupture a contracted fibrous capsule surrounding the implant, the hands of the operator gripping the handles of the compressor being shown in broken lines.
Figure 5:
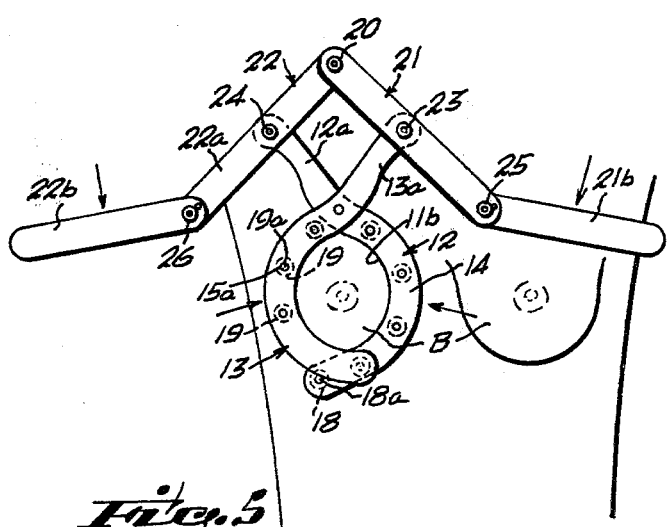
FIG. 5 is a view similar to FIG. 4 but showing the compressor in a partially closed position after rupturing the fibrous capsule.

Pincers 11 is formed as a pair of blades 12 and 13 pivotally connected at midportion thereof by pivot pin 16 in scissor-fashion. Blades 12 and 13 have business ends or jaws 14 and 15, respectively, which are semi-circular in contour to define an opening 11a of substantially circular configuration when in an open position, as seen in FIGS. 1 and 4, and closing to define an opening 11b of oval configuration, as seen in FIG. 5. Blade 12 is shown to be located on the rearward side of pincers 11 with jaw 14 thereof carrying a plurality of grippers 18 extending perpendicularly in a rearward direction and herein shown as five in number substantially equally spaced along the arcuate length of jaw 14. Blade 13 is located on the front side of pincers 11 with opposing jaw 15 also carrying a plurality of grippers 19 extending rearwardly and parallel to grippers 18 but fewer in number, namely three, being located only along half the arcuate length of jaw 15 adjacent pivot pin 16, leaving the other half of jaw 15 free of obstruction to close in front of jaw 14 as will be clear from FIGS. 4 and 5 in the manner hereinafter more fully described.

Grippers 18 and 19 may each be made of rod stock, preferably circular in cross-section, of a suitably sturdy plastic material, such as a nylon, for example, "Delrin", providing the desired rigidity, and may be suitably secured in parallel relation by threaded ends 18a and 19a engaging threaded openings 14a and 15a formed in jaws 14 and 15, respectively. As seen in FIG. 2, each of the grippers 18 and 19 has a rounded free end 18b and 19b, respectively, all terminating in a common plane, grippers 19 being longer that grippers 18 to provide for the thickness of rearwardly positioned jaw 14.

The actuating sections 12a and 13a of blades 12 and 13 are seen to be pivotally mounted at their ends on proximal sections 22a and 21a of lever arms 22 and 21 by pivot pins 24 and 23, respectively. Each of the pivot pins 23 and 24 is located at a distance from pivot pin 20 equal to each other and to about ¼ the total length of lever arms 21 and 22, which arms are seen to be identical in size and configuration but arranged as mirror images of each other. Likewise, the distances measured along the blade actuating sections 12a and 13a between pivot pins 23 and 24 and pivot pin 16 are equal to each other and on the order of the distances between pin 20 and pins 23 and 24. As shown in the preferred embodiment herein, the distances measured along actuating sections 12a and 13a slightly exceed those measured along lever arms 21 and 22.

Figure 3:
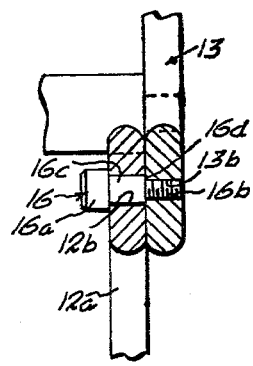
FIG. 3 is an enlarged sectional view taken on line 3—3 in FIG. 1 showing details of the pivoted connection.

While any suitable structure may be adopted for pivot pins 16, 20, 23 and 24, those herein provided are all similar and a representative detailed illustration thereof is shown in FIG. 3 wherein pivot pin 16 is formed as a threaded bolt having a head 16a which may be formed to accommodate an Allen wrench, a threaded end 16b and a non-threaded intermediate shank portion 16c between head 16a and threaded end 16b providing a shoulder 16d. One of the pivoting members, for example, blade 13 has a threaded opening 13b for engaging threaded end 16b, and blade 12 has a non-threaded opening 12b sized to receive shank portion 16c as a bearing-fit therein. When shoulder 16d is tightened against blade 13 fixedly attaching bolt 16 thereto, head 16a is spaced from shoulder 16d to retain blade 12 in position substantially against blade 13 but permitting sufficient freedom for rotation of blade 12 on shank portion 16c to effect the pivoting action between blades 12 and 13.

Lever arms 21 and 22, instead of being straight, may have end sections 21b and 22b, respectively, curved or bent laterally with respect to proximal sections 21a and 22a, that is, away from pincers 11, to provide adequate clearance therefrom for gripping by the hands of the operator and especially when lever arms 21 and 22 are brought toward each other to fully close jaws 14 and 15 as will be apparent from FIG. 5. While lever arms 21 and 22 may be formed as an integral structure to provide the angular or curved relation between proximal sections 21a and 22a and end sections 21b and 22b, respectively, in the embodiment shown herein lever arms 21 and 22 are each formed as a two-piece structure of straight bar stock with end sections 21b and 22b suitably joined in angular relation to proximal sections 21a and 22a, respectively. While suitable rivets or other fasteners may be used, the interconnection here shown comprises pin 25 between sections 21a and 21b and pin 26 between sections 22a and 22b. Pins 25 and 26 are similar in structure and coaction to pins 16, 20, 23 and 24 and cooperate with suitable roll pins 27 and 28 extending through aligned openings formed in sections 21a, 21b and 22a, 22b adjacent pins 25 and 26, respectively, roll pins 27 and 28 serving to lock the sections against relative rotation and in the desired predetermined angular relation.

Blades 12 and 13, proximal sections 21a and 22a and end sections 21b and 22b may all be made of a suitable lightweight metal, such as aluminum, and all be of similar thickness for assembly into compressor 10 in which these parts are shown to be arranged in three parallel planes. Thus, blade 12 lies in the rearmost plane, blade 13, end section 21b and proximal section 22a all lie in an intermedite plane, while proximal section 21a and end section 22b lie in a frontal plane. Alternatively, end sections 21b and 22b may both be positioned either on the front or on the rear sides of their respective proximal sections 21a and 22a.

The practical utility and operation of manually operated compressor 10 will now apparent. After being flipped over on a horizontal axis from the position shown in FIG. 1 to that shown in FIGS. 4 and 5, compressor 10 is held by the operator's right and left hands gripping end sections 21b and 22b, respectively, adjacent the free ends thereof as indicated in broken lines. The patient may either stand erect against a wall or lie on a table in a supine position. With arms 21 and 22 held outstretched to dispose jaws 14 and 15 in a substantially open position, rounded free ends 18b and 19b of grippers 18 and 19 are placed against the rib cage so that the breast B, to be operated on, extends into the substantially circular opening 11a defined by grippers 18 and 19. As lever arms 21 and 22 are brought downwardly and toward each other in the directon of the arrows shown in FIG. 5 to reduce the angle therebetween, jaws 14 and 15 begin to close, bringing grippers 18 and 19 toward each other to circumferentially engage the breast B, particularly at the base of the implant. Now, while maintaining the gripper free ends 18b and 19b against the rib cage, force exerted by the operator's upper arms and shoulders to end sections 21b and 22b is applied through jaws 14 and 15 to grippers 18 and 19, respectively, bringing inward radial pressure circumferentially to bear upon the contracted fibrous capsule enclosing the implant. In this manner, aided by the mechanical advantage of at least 2 to 1 of compressor 10 achieved by the relative proportions of pincers 11 and lever arms 21 and 22 and particularly the approximate 4 to 1 ratio of the distances between pivot pin 20 and pivot pins 23 and 24 to the overall effective length of lever arms 21 and 22, sufficient force is easily provided by the operator to achieve the initial "pop" signalling rupture of the fibrous capsule while being able to maintain complete control of his movements to substantially reduce the likelihood of rupturing the coating or skin of the implant. During his initial "pop", rupturing procedure, a feel of the implant within the breast has been found to be transmitted through pincers 11 and lever arms 21 and 22 to the operator's hands, thereby aiding him in manipulation of compressor 10. After the initial "pop", the operator may complete the procedure by performing the follow-through twist by direct manipulation of the breast to ensure complete release of the implant.

To avoid causing discomfort by being relatively cold to the touch when applied to the patient's skin, grippers 18 and 19, as hereinbefore described, are made of nylon or the like material chosen for its low heat conductivity. It is contemplated, as an alternative and within the scope of the invention, to fashion grippers 18 and 19 of the same lightweight metal as the other elements. In such case and where avoidance of the cold-to-the-touch discomfort is desired, grippers 18 and 19 may be coated with a suitable latex having heat insulating properties.

The manually operated compressor herein disclosed is seen to achieve the several objects of the invention and to be well adapted to meet conditions of practical use. As various possible embodiments might be made of this invention, and as various changes might be made in the disclosed compressor, it is to be understood that all matters herein set forth and shown in the accompanying drawing are to be interpreted as illustrative and not in a limiting sense.

What is claimed is:

1. A manually operated compressor for achieving the initial rupturing "pop" in performing the closed compression technique to alleviate a contracted fibrous capsule condition of an augmentation mammaplasty implant comprising a pair of actuating lever arms pivotally interconnected at one end thereof and disposed in angular relation and having opposite free ends adapted as handles for gripping and operating the compressor, a pincers mounted on and between said lever arms for actuation thereby, said pincers comprising a pair of centrally pivoted blades each having a semi-circular shaped jaw, and a plurality of elongated grippers mounted on each of said jaws to project perpendicularly from a rear, breast facing, side of the jaws and arranged in parallel spaced relation, said jaws and grippers defining a substantially circular opening sized to circumferentially fit the base of the implant of a patient's breast when the jaws are in open position, the rear facing jaw having the grippers spaced along the length thereof, the other, front facing, jaw having the grippers spaced along substantially half the length of the jaw adjacent the central pivot of the pincers to permit closing of the jaws to reduce the area of said opening enabling circumferential compressive force to be exerted on the patient's breast at the base of the implant when the breast is positioned within the confines of the grippers.

2. The manually operated compressor defined in claim 1 in which said actuating lever arms and pincers are constructed and arranged to provide a mechanical advantage to the closing of said jaws and grippers when manual force is applied to said handles to reduce the angle between said lever arms.

3. The manually operated compressor defined in claim 2 in which each of said pivoted blades has an actuating section opposite said jaw, each actuating section being pivoted at an end thereof to one of said lever arms at a predetermined distance from said lever arm pivotal interconnection as said pincer mounting, the distances measured along said actuating sections between said end pivot and said central pivot and said predetermined distances being substantially of the same order, and the ratio of said predetermined distance to the overall effective length of said lever arm being approximately 1 to 3½ providing said mechanical advantage.

4. The manually operated compressor defined in claim 1 in which each of said grippers has a rounded free end, said ends being in substantially coplanar relation with each other.

5. The manually operated compressor defined in claim 4 in which each of said grippers has a surface of low heat conductivity to avoid cold-to-the-touch discomfort.

6. The manually operated compressor defined in claim 1 in which each of said actuating lever arms has an end portion including said handle bent laterally away from said pincers to provide clearance therefrom for gripping said handles when said lever arms are brought toward each other to fully close said jaws.

7. The manually operated compressor defined in claim 6 in which each of said lever arms is formed as a two-piece structure of bar stock interconnected in angular relation to provide said lateral bend.

* * * * *